United States Patent
Chen et al.

(10) Patent No.: US 9,326,888 B2
(45) Date of Patent: *May 3, 2016

(54) SYSTEM AND METHOD TO REGULATE TEMPERATURE

(75) Inventors: Jane Chen, San Francisco, CA (US); Linus Liang, Saratoga, CA (US); Rahul A. Panicker, Bangalore (IN); Razmig Hovaghimian, Glendale, CA (US); Naganand Murty, Bangalore (IN)

(73) Assignee: Embrace, San Francisco, CA (US)

(*) Notice: Subject to any disclaimer, the term of this patent is extended or adjusted under 35 U.S.C. 154(b) by 351 days.

This patent is subject to a terminal disclaimer.

(21) Appl. No.: 13/603,380

(22) Filed: Sep. 4, 2012

(65) Prior Publication Data

US 2012/0330388 A1    Dec. 27, 2012

Related U.S. Application Data

(63) Continuation of application No. 12/454,185, filed on May 12, 2009, now Pat. No. 8,257,417.

(60) Provisional application No. 61/052,554, filed on May 12, 2008.

(51) Int. Cl.
*A61F 7/00* (2006.01)
*A61F 7/02* (2006.01)

(52) U.S. Cl.
CPC .............. *A61F 7/02* (2013.01); *A61F 7/0097* (2013.01); *A61F 7/0241* (2013.01); *A61F 2007/0001* (2013.01); *A61F 2007/0095* (2013.01); *A61F 2007/0225* (2013.01); *A61F 2007/0238* (2013.01); *A61F 2007/0292* (2013.01)

(58) Field of Classification Search
CPC . A61F 7/02; A61F 7/0097; A61F 2007/0241; A61F 2007/0292

USPC .......................................... 607/104, 108, 112
See application file for complete search history.

(56) References Cited

U.S. PATENT DOCUMENTS

| | | | |
|---|---|---|---|
| 4,856,294 A * | 8/1989 | Scaringe et al. ............. 62/259.3 |
| 5,415,222 A * | 5/1995 | Colvin et al. ................... 165/46 |
| RE35,586 E | 8/1997 | Manker |
| 5,804,266 A * | 9/1998 | Salyer .......................... 428/35.2 |
| 6,009,576 A * | 1/2000 | Gramme et al. .............. 5/413 R |
| 6,120,530 A * | 9/2000 | Nuckols et al. ............... 607/108 |
| 6,185,742 B1 * | 2/2001 | Doherty .............................. 2/81 |
| 6,189,149 B1 * | 2/2001 | Allen ................................ 2/102 |
| 6,298,907 B1 * | 10/2001 | Colvin et al. ................... 165/46 |
| 6,652,771 B2 * | 11/2003 | Carn ............................... 252/70 |
| 6,855,410 B2 * | 2/2005 | Buckley .................... 428/311.11 |
| 7,744,640 B1 * | 6/2010 | Faries et al. ................... 607/109 |
| 8,012,191 B2 * | 9/2011 | von Hoffmann et al. ..... 607/114 |
| 8,834,548 B2 * | 9/2014 | Liang ................... A61F 7/0241 219/385 |
| 2002/0164473 A1 * | 11/2002 | Buckley ...................... 428/308.4 |
| 2002/0164474 A1 * | 11/2002 | Buckley ...................... 428/308.4 |
| 2003/0109911 A1 * | 6/2003 | Lachenbruch et al. ....... 607/112 |
| 2007/0055330 A1 * | 3/2007 | Rutherford .................... 607/114 |
| 2007/0083251 A1 * | 4/2007 | von Hoffmann et al. ..... 607/114 |
| 2009/0229593 A1 * | 9/2009 | Komiya ...................... 126/263.01 |
| 2010/0280581 A1 * | 11/2010 | Cushman et al. ............. 607/112 |
| 2012/0305231 A1 * | 12/2012 | Liang et al. ................... 165/287 |

* cited by examiner

*Primary Examiner* — Kaitlyn Smith

(74) *Attorney, Agent, or Firm* — Levine Bagade Han LLP

(57) ABSTRACT

A system and method for thermal regulation, the system comprising a bedding element that is configured to enclose at least a part of a living being or other object. The system further comprising a temperature regulation element that is included in the bedding element and that includes a phase change material which changes between a liquid phase and a solid phase within the desired temperature range.

19 Claims, 10 Drawing Sheets

SYSTEM AND METHOD TO REGULATE TEMPERATURE

PRIORITY INFORMATION

This patent application is a continuation of U.S. patent application Ser. No. 12/454,185, filed on May 12, 2009, (now U.S. Pat. No. 8,257,417), which claims the benefit of priority to U.S. Provisional Patent Application Ser. No. 61/052,554, filed on May 12, 2008. The Ser. No. 12/454,185 application is hereby incorporated by reference.

TECHNICAL FIELD

This invention relates generally to the field of temperature regulation, including a new and useful system and method to regulate the temperature of infants and other humans, as well as animals or other inanimate objects.

BACKGROUND

The average temperatures of locations throughout the world vary significantly. In addition, extreme temperatures, from peak high to peak low, also vary dramatically throughout the world. For example, recorded temperatures on Earth range from 56.7° C. (134° F.) in Death Valley, Calif. to −89.2° C. (−128.6° F.) in Vostok Station, Antarctica. The extreme temperatures of a single location may also represent a wide temperature range. For example, many locations throughout the world experience high temperatures in summer and cold temperatures in winter.

Despite Earth's varying climates and extreme temperature differences, animals, birds, and even humans inhabit almost every corner of the planet. This proliferation of habitat is astonishing when considering that many animals and birds, and all humans, must maintain thermal homeostasis, and constantly regulate their body temperatures to within only a few degrees Celsius.

The average normal human body temperature varies between about 36.12° C. and 37.5° C. (96.8-99.5° F.). If a person's body temperature rises only 1° C. to 38° C. (100.4° F.), that person may begin to sweat and feel very uncomfortable. At an increase of 3° C. to 40° C. (104° F.), fainting, dehydration, weakness, vomiting, headache, dizziness, and profuse sweating may occur. An increase of 6° C. from normal to 43° C. (109.4° F.), normally results in death.

Likewise, the human body does not fair well in extreme cold. At a decrease of 1° C. to 36° C. (96.8° F.), a person may start to shiver. At a decrease of 3° C. to 34° C. (93.2° F.), severe shivering, loss of movement of the fingers, blueness and confusion may set in. At a decrease of 9° C. to 28° C. (82.4° F.), severe heart rhythm disturbances are likely and breathing may stop at any time.

While temperature ranges for other homeothermal animals may vary from those of humans, an animal's need to thermally regulate its body temperature is similar.

When temperatures are extreme, maintaining a constant body temperature can be difficult even for grown healthy adults. Sleeping outside in cold conditions, such as on a camping trip, may require large sleeping bags or heaters. Playing winter sports may require layers of thermal protection such as gloves, hats and coats. Army soldiers operating in the field under extreme conditions often experience hypothermia or heat exhaustion.

Numerous unsuccessful attempts have been made to address problems associated with regulating body temperature. For example, electric blankets that incorporate resistive heating elements in order to produce extra heat are well known. However, numerous problems exist with typical electric blanket designs. For example, electric blankets require electricity which is often not available during emergencies or in rural areas. Electric blankets also do not distribute heat evenly and may require sophisticated electronics to regulate heat, if regulated at all. Furthermore, the resistive heating elements that are typically woven into the electric blanket may create a fire hazard. In addition, the heating system in electric blankets may be delicate because the small gauge wires that are often used to increase resistance and comfort are susceptible to breaking.

Other devices exist to regulate body temperature. However, a major problem in any of these devices is the complexity of the components that actually control the temperature. U.S. Pat. No. 4,856,294 to Scaringe et al. discloses a device designed to keep the body cool through the use of heat exchange materials that are effectively endothermic in a temperature range that is below normal body temperature. Scaringe discloses a micro-climate cooling vest that uses a heat transfer material that changes phase from solid to liquid within the practical range of 60°-90° F. to cool the body of workers in high temperature environments. The vest is filled with the heat transfer material through fill ports. The entire vest is then placed in an environment capable of freezing the heat transfer material. Once sufficiently cooled, the vest is worn.

While Scaringe discloses the use of an endothermic heat transfer material to cool the body, the design of the micro-climate vest still leaves many problems unsolved. For example, the vest leaves large portions of the body unprotected from the environment including the legs and head which typically generate a majority of body heat and which may need cooling. In addition, vests may be difficult to put on infants or small animals and may not attain the desirable snug fit on their small bodies. Also, it is unlikely that a person in the wilderness or in other extreme conditions such as a soldier in battle would have the necessary heat transfer material to fill the vest. Even if the vest were pre-filled with the heat exchange material, the freezer necessary to prepare the vest for use would likely not exist in environments such as the wilderness, a battlefield, or in the rural areas of developing countries. Furthermore, placing the entire vest in a freezer environment to prepare the vest for use may cool other portions of the vest disproportionately from the heat exchange material, making those portions of the vest much colder than desired.

In the human body, as well as in the bodies of animals, the nervous regulating mechanism regulates body temperature by controlling the body's reaction to temperature. For example, the nervous regulating mechanism may cause goose bumps to form in response to cold, or may cause the body to sweat in response to heat.

While temperature regulation may be difficult even for healthy adults, infants may be especially susceptible to external temperature. The temperature inside a mother's womb is 38° C. (100.4° F.). As soon as an infant leaves the warmth of the womb at birth, the infant is exposed to a much colder environment and immediately starts losing heat. Because an infant cannot regulate its body temperature as well as an adult, the infant cools down and heats up much faster than an adult and therefore, is able to tolerate only a limited range of environmental temperatures.

Babies who are born prematurely, with low-birth-weight (LBW), or weak and ill-developed, may have a particularly difficult time regulating body temperature because their nervous regulating mechanisms are often underdeveloped. If heat loss is not prevented and is allowed to continue, such babies will develop hypothermia. A hypothermic baby, especially if it is small, sick, or is of LBW, is at increased risk of developing health problems and of dying.

Twenty million premature and LBW babies susceptible to thermoregulation problems are born every year around the world. In developed countries, LBW babies are placed in incubators to regulate their temperature. Typical incubators are very expensive, costing thousands of US dollars. Such incubators require active electrical connections and may require delicate electronics. They are also heavy and cumbersome. These factors typically limit the use of such incubators to the urban hospitals of well developed countries and prevent typical incubators from being portable.

Unfortunately, eighty percent (80%) of LBW babies are born in rural areas of developing countries where typical incubators either do not exist or are hardly available. In India alone, for example, a third of all babies born are LBW. Three and a half (3.5) million LBW babies die each year, while those who survive often develop life-long health problems like the early onset of diabetes, heart disease and low IQ.

As mentioned above, traditional incubators cost thousands of dollars, and are available primarily only in urban hospitals. Even where available, incubators in developing countries are often in disrepair. Regardless, most rural parents cannot afford to get their babies to these urban hospitals. In summary, many LBW babies effectively have no access to incubators.

To address the limited access to incubators in the rural areas of developing countries, a low cost incubator design to help the needs of LBW babies was proposed by MIT students. MIT students proposed an incubator that included a small dome tent structure suspended over a double layered floor. The floor contained an opening to receive a heating mattress. The heating mattress incorporated a phase change material (PCM) to passively regulate temperature. Although costing far less than incubators used in hospitals, the MIT incubator design has various drawbacks.

For example, in the dome tent structure of the MIT incubator design, the baby can not be held by the parent while in the incubator. If the baby needs comforting or nursing, the baby must be removed from the incubator and risk exposure to temperature change in order to do so. In addition, because the baby is not secured within the dome tent structure and is free to roll around, it is possible, if left unsupervised, for the baby to roll out and lose the environmental protection the dome tent provides. Furthermore, the dome tent structure does not provide any warmth for the child outside of the heat coming from the heating mattress. This makes it an inefficient design and susceptible to rapid cooling if the heating mattress fails. Also, the dome tent structure is not a rugged design suitable for longevity and the harsh environments associated with transport. The rods used in the tent structure could be easily broken or the fabric used on the outside of the tent could be easily torn or crumpled.

In addition to the thermal regulation help an incubator provides, LBW babies often need the immediate medical attention of a doctor. Therefore, the ability to transport the baby while remaining in the incubator is an important factor in a solution for infants born in rural areas. The structure of the MIT dome tent design is not rigid enough to support the weight of the baby during transport. In addition, the dome tent design does not conform closely enough to the shape of the baby to allow the baby and the dome tent structure to be easily carried together. Therefore, attempts to transport the dome tent while the baby is inside could lead to injury.

Infant or baby warming devices that include super-cooled inorganic PCMs have also been proposed. Super-cooling is the cooling of a liquid or saturated solution below its freezing point without crystallization taking place. Super-cooling is possible because of the lack of solid particles around which crystals can form. Crystallization rapidly follows the introduction of a small crystal (seed) or agitation of the super-cooled solution. However, the final temperature attained by the super-cooled solution, and thus the amount of heat released during the exothermic phase change of crystallization, depends on the temperature prior to activation.

The Cooper Surgical Transwarmer heat source, as disclosed in US Reissue Pat. No. 35,586, is an infant warming mattress aimed at temperature regulation. The Transwarmer uses a super-cooled salt solution of sodium acetate (inorganic PCM) that may be activated by a button and that subsequent to activation, releases heat in an exothermic reaction (heat of crystallization). Because of their dependence on the initial temperature, inorganic PCM's that are super-cooled, such as those in the Transwarmer, may not have a predictable and stable final temperature. The unpredictability of temperature is dangerous and may cause burning. In addition, warmers using inorganic PCM's like the Transwarmer, do not maintain their temperature for very long periods of time, i.e., typically only around two hours. Furthermore, devices like the Transwarmer are single use devices making them impractical for use outside of hospitals where they can not be stocked.

In view of the foregoing, a need exists for an improved thermal regulation device and method that addresses or at least ameliorates one or more of the problems associated with existing thermal regulation designs.

SUMMARY

In view of the foregoing, an object according to one aspect of the present invention is to provide an improved system for regulating temperature within a desired temperature range. The system for regulating temperature may be used for any thermal regulation need but preferably, the system for regulating temperature is suitable for use in thermally regulating an infant or baby. To this end, a system for regulating temperature within a desired temperature range is provided comprising a bedding element that is configured to enclose at least a part of a living being. The system has a temperature or thermal regulation element that is included in the bedding element and that includes a phase change material which changes between a liquid phase and a solid phase within the desired temperature range.

In a preferred embodiment, the temperature regulation element is separable from the system and can be completely removed from the bedding element to allow reheating. In one embodiment, the temperature regulation element is a flexible pouch and the phase change material is microencapsulated and disposed within the pouch with a liquid. In yet another embodiment, the phase change material may be disposed within the pouch in bulk form instead of microencapsulated.

The system may further comprise a separate recharging unit, the recharging unit shaped to be thermally coupled to the temperature regulation element. The recharging unit can heat the temperature regulation element to a desired temperature and then be decoupled from the temperature regulation element. The temperature regulation element can then be placed back into the bedding element.

In another embodiment, the recharging unit may be a hollow body capable of holding a liquid. The recharging unit can be filled with hot or cold water and coupled to the temperature regulation unit to recharge it. Alternatively, the recharging unit may be an electric heater. More than one temperature regulation element may be used so that when combined with the recharging unit, one temperature regulation unit may be recharged while the other is in use, thereby providing continuous temperature or thermal regulation.

The system for regulating temperature may further comprise a fastening means disposed on the bedding element, wherein the fastening means attaches a foldable portion of the bedding element to form an interior area. Preferably the bedding element has at least two compartments. The first compartment, or interior area, holds or encloses at least part of an infant, baby, animal or other item to be thermally regulated, and the second compartment, or pouch, holds the temperature regulation element. In the preferred embodiment, the first compartment is held closed by the fastening means so that the first compartment can be opened up and access to the infant or body to thermally regulate can be attained.

According to a further embodiment, the interior area is proximately shaped to fit an infant or other body to be thermally regulated. When the thermal regulation system is used to incubate a human infant, it may be preferable to shape the interior area to conform to the infant's body. Sections to accommodate arms, legs, and other shapes may be formed into the interior area to better conform the interior area to the infant's body. Additionally, a hood component may be disposed at an end of the interior area to receive and thermally regulate the infant's head. The hood component may be adjustable with respect to the end of the interior area.

In another embodiment, the system further comprises straps attached to the bedding element which are configured to enable a caregiver to wear or carry the system.

According to yet another embodiment, the phase change material changes phase in the range between 34 degrees Celsius and 38 degrees Celsius, which is the preferred temperature range for a human infant.

According to a further embodiment, the phase change material of the system for temperature regulation is composed of an organic material. Organic material is preferable because it maintains a more stable temperature, increases reusability, and reduces the chance of injury and the risks associated with super-cooling such as burning. In one embodiment, the phase change material may be n-eicosane, Tetradecanol or an eutectic mixture.

In yet another embodiment the phase change material is a combination of organic and inorganic materials. This combination provides the stability of the organic material's temperature control while allowing the accelerated recharging ability found in inorganic phase change materials.

In a further embodiment, a system for regulating the temperature of a human infant within a desired temperature range comprises a bedding element that is configured to substantially enclose the human infant and that includes an inner layer, an outer layer and a pouch between the inner layer and the outer layer. The temperature regulation element is releasably contained in the pouch and includes a phase change material which changes between a liquid phase and a solid phase within the desired temperature range. The system also includes a temperature indicator that is thermally coupled to the temperature regulation element and that is visible on the outside of the bedding element. Furthermore, the system has a recharging unit that is separate from the bedding element and is configured to receive and heat the temperature regulation element when the temperature regulation element is separated from the bedding element.

In yet another embodiment, the material of the inner layer is thermally conductive. The outer layer, having good insulating properties, can insulate both the thermal regulation element and the infant.

As described more fully below, the system for regulating temperature within a desired range and methods for using the same may readily and cost effectively be used for thermal regulation. Further aspects, objects, desirable features, and advantages of the thermal regulation system and methods disclosed herein will be better understood from the detailed description and drawings that follow in which various embodiments are illustrated by way of example. It is to be expressly understood, however, that the drawings are for the purpose of illustration only and are not intended as a definition of the limits of the claimed invention.

BRIEF DESCRIPTION OF THE DRAWINGS

FIGS. 2A and 2B illustrate cross-sections of embodiments of the thermal regulation system.

FIG. 4B illustrates an exterior view with a portion or strip of the bedding element hinged open to show the temperature regulating element.

FIG. 4C illustrates an exterior view with a portion or strip of the bedding element hinged open to show the temperature regulating element.

DETAILED DESCRIPTION

The following description of preferred embodiments of the invention is not intended to limit the invention to these embodiments, but rather to enable a person skilled in the art to make and use this invention.

Figure 1:
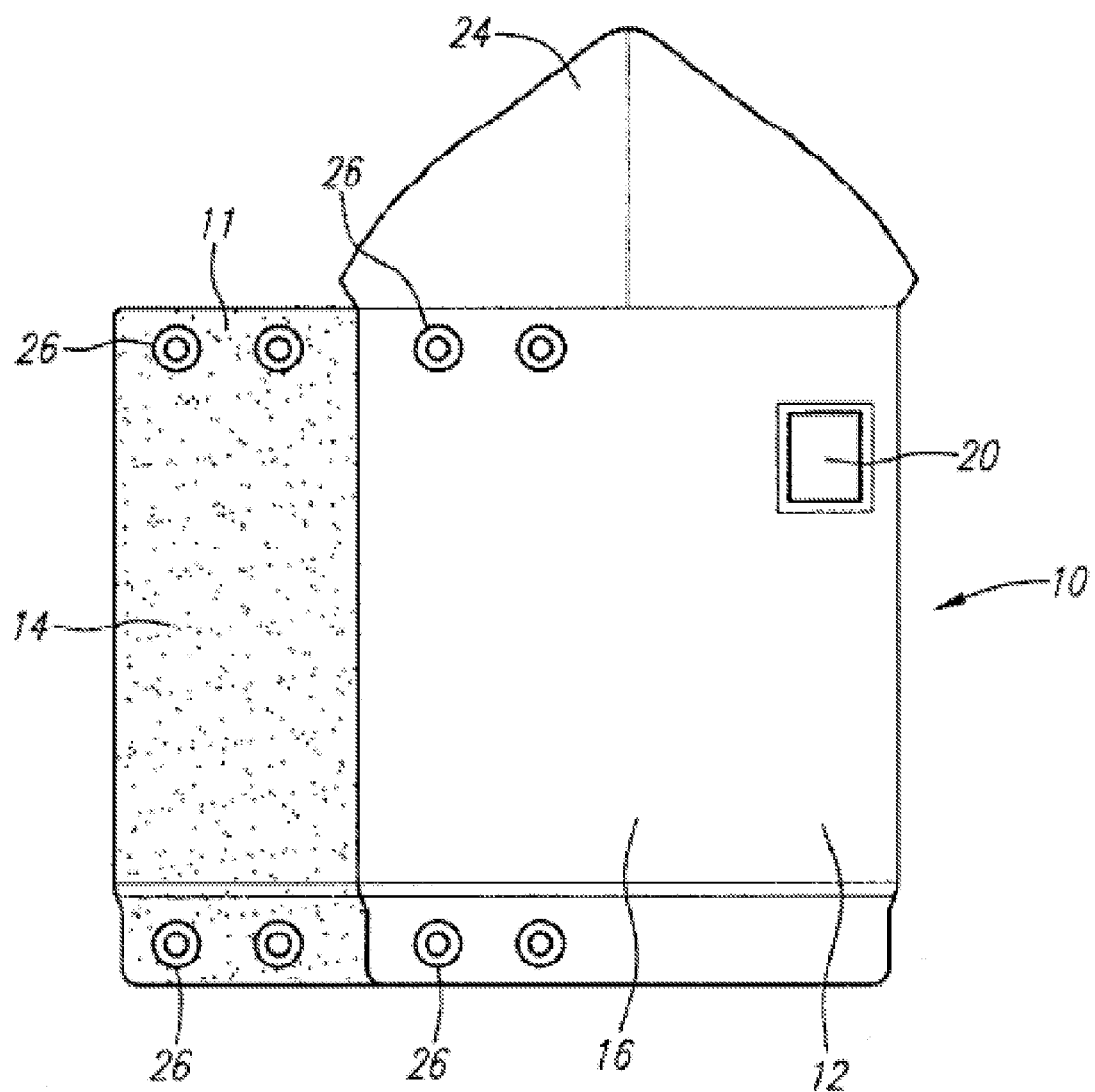
FIG. 1 illustrates a rear exterior view of the bedding element of a thermal regulation system according to a preferred embodiment.

FIG. 1 illustrates a rear exterior view of the bedding element of a thermal regulation system according to a preferred embodiment. As shown in FIG. 1, the system 10 of the preferred embodiments includes a bedding element 12. The bedding element 12 can be of various different shapes or designs. The bedding element 12 may be designed as a sack, bag, pouch or other compartmental design that may hold an infant, baby or other body or item whose temperature is to be thermally regulated.

While the bedding element 12 may have a built in compartment to hold an infant, baby or other body or item, preferably the bedding element 12 is a blanket, comforter, or warmer and can wrap around, fold over and/or otherwise enclose or substantially enclose the infant or other body to be thermally regulated. In such a foldable configuration the bedding element 12 may have a body portion in which the infant is laid and at least one foldable portion that may fold over and enclose the infant in an interior. While the bedding element 12 preferably provides the comfort associated with sleeping, the bedding element 12 is not limited to uses involving sleep.

As mentioned above, FIG. 1 illustrates the rear exterior of system 10. Though not explicitly shown in FIG. 1, the bedding element 12 may comprise a contiguous blanket or other comforting item that extends around the front of system 10, and includes an extra length comprising flap 11. FIG. 1 shows flap 11 in an extended position, but flap 11 may be folded over such that one or more fasteners 26 (shown as concentric circles on flap 11) may engage fasteners (also shown as concentric circles) on the back of bedding element 12. When flap 11 is snapped to or otherwise connected to the back of bedding element 12, the infant is preferably snugly enclosed in system 10.

Figure 2:
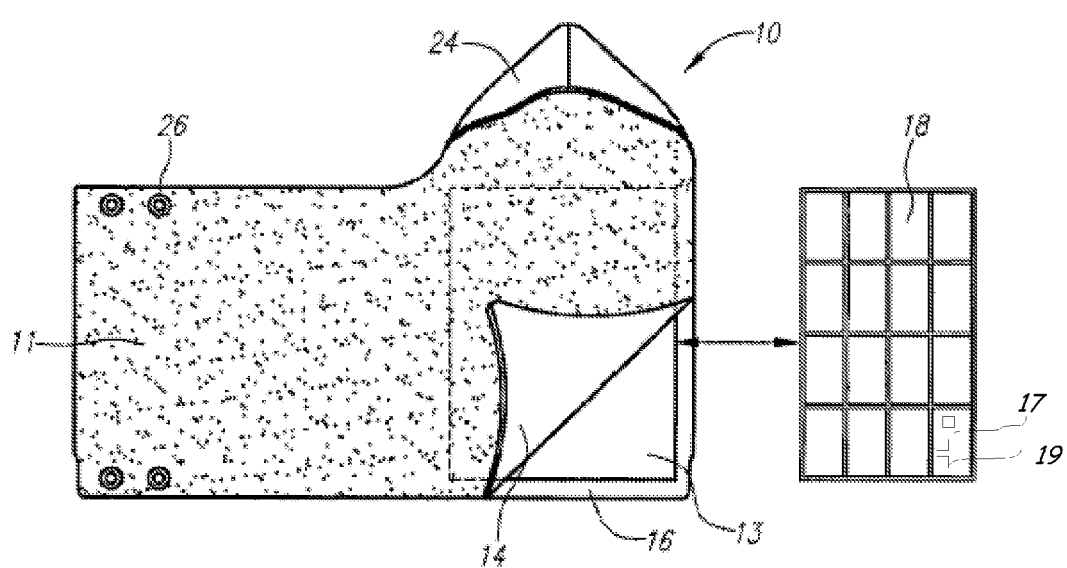
FIG. 2 illustrates a front view of a thermal regulation system with the bedding element extended or unfolded according to a preferred embodiment and FIG. 2A and FIG. 2B illustrate cross-sections of embodiments of the thermal Regulation system.

FIG. 2 illustrates a front view of a thermal regulation system with the bedding element extended or unfolded according to a preferred embodiment. In use, the extended part or foldable portion of bedding element 12 may be folded over the infant to form an interior. The flap 11 may again be folded over and connected to the rear of system 10 with fasteners 26 as described in connection with FIG. 1.

The use of a blanket or sack such as bedding element 12 is preferred rather than an article of clothing because bedding element 12 can completely enclose the infant or other body to be thermally regulated and therefore, better regulate temperature. By more fully enclosing the infant or body to be thermally regulated, the bedding element 12 provides additional thermal insulation. Additional thermal insulation is preferable because it more efficiently retains the heat of the system 10 during normal operation and when the heating means fails or is removed.

The flexibility of bedding element 12 also preferably allows it to accommodate various sized bodies. In addition, bedding element 12 can be made completely collapsible for ease of shipping, distribution or storage. Also, bedding element 12 can be made extremely durable so as to last a long time in harsh conditions. For example, it is preferred that bedding element 12 may be stepped on or kicked or squashed without damage whereas a less flexible structure would break. The bedding element 12 is preferably washable so that if it gets dirty, it can be cleaned.

In addition, a bedding element design can conform to the infant's body and is light and flexible and thus allows both the infant and bedding element 12 to be easily carried together. This makes the system 10 extremely portable and therefore advantageous for thermally regulating infants born in rural areas that need to be transported to a hospital or just generally need to remain close to the mother or other caregiver.

Figure 3:
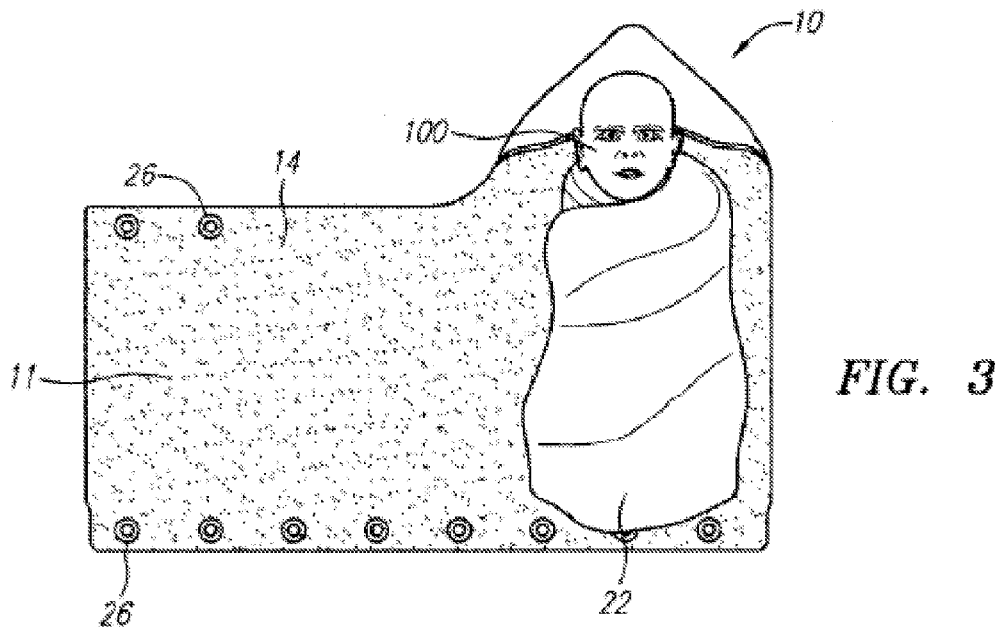
FIG. 3 illustrates a view of a thermal regulation system with an infant training manikin placed on the extended or unfolded bedding element.

FIG. 3 illustrates a view of a thermal regulation system with an infant training manikin placed on the extended or unfolded bedding element. As shown in FIG. 3, the system 10 may be preferably designed to thermo-regulate an infant 100 and more specifically is preferably designed to thermo-regulate infants in developing countries and rural and/or impoverished areas. When used to thermally regulate an infant 100, the system 10 may be referred to as an incubator.

Although going forward the system 10 will be described at times in relation to thermo-regulating an infant, the system 10 may be used to thermo-regulate babies and children of various ages, as well as adults such as soldiers or campers. The system 10 may also be used to thermo-regulate or incubate animals. In addition, the system 10 may be used in any suitable environment and for any suitable reason including the thermo-regulation of inanimate objects. For example, the system 10 could be used as a type of drink koozie to keep liquids in a container at a preferred temperature.

In FIG. 3, the bottom of bedding element 12 may include connectors that engage matting connectors when the extended portion is folded over. These connectors help enclose the bottom of bedding element 12 to prevent heat loss and also more snugly secure the infant or other body to be thermally regulated. Alternatively, the bottom may be narrower or include a drawstring or an elastic band to help enclose the bedding element 12.

Figure 3A:
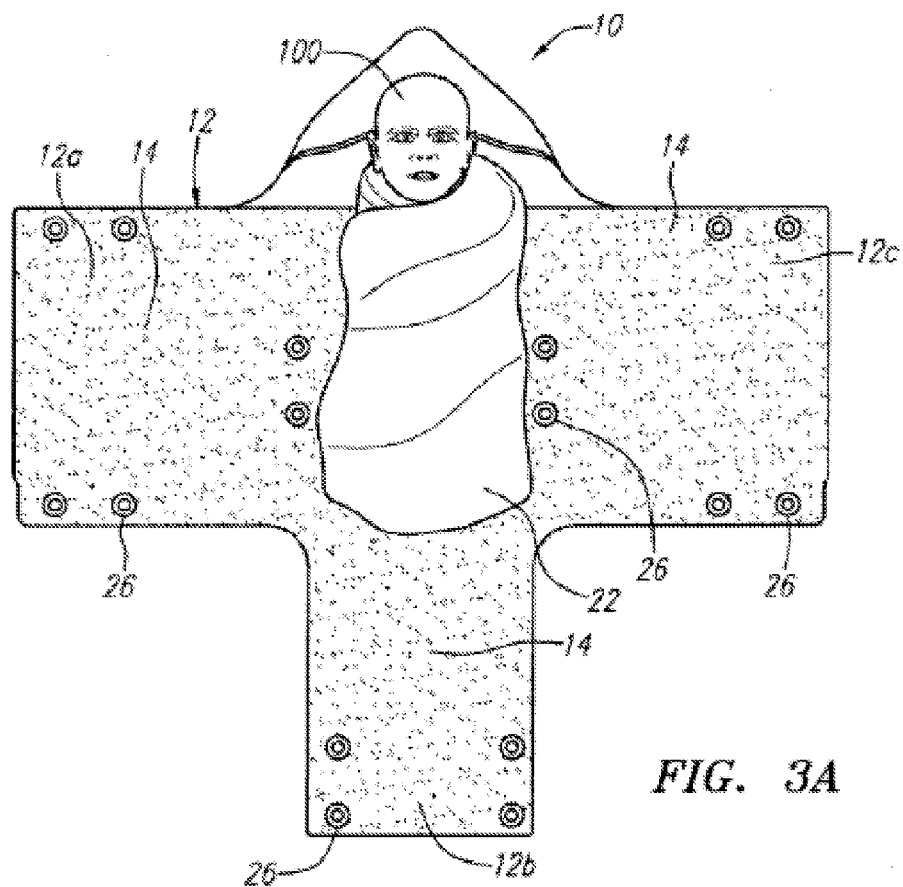
FIG. 3A illustrates a view of a thermal regulation system with an infant training manikin placed on the body portion of the bedding element with the foldable portions extended.

FIG. 3A depicts an alternative embodiment of system 10. As shown in FIG. 3A, the bedding element 12 may include flaps or foldable portions 12a, 12b, and 12c. In use, the infant 100 (or other body to be thermally regulated), is placed on the body portion of the bedding element 12, and flaps or foldable portions 12a, 12b, and 12c are successively folded over to enclose the infant from each side in an interior. In FIG. 3A three flaps at 90 degree angles are shown. However, any number of flaps, including flaps at angles other than 90 degrees, may be used in a similar flower pedal design. In a preferred embodiment, bottom flab 12b is folder over first, followed by flaps 12a and 12c.

Figure 4:
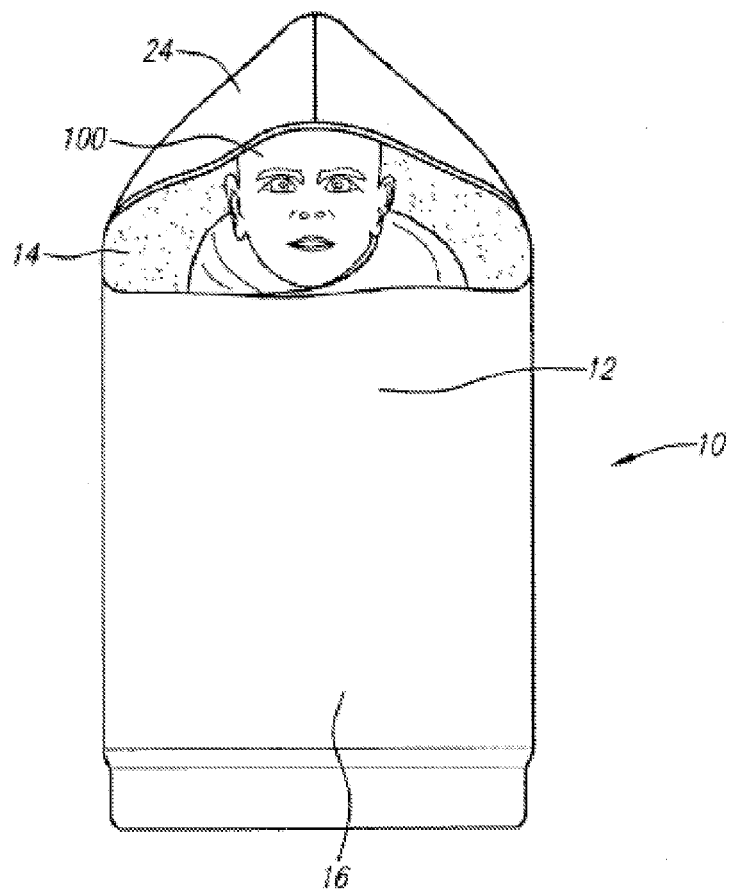
FIG. 4 illustrates an exterior view with an infant training manikin inside the bedding element.

FIG. 4 illustrates an exterior view with an infant training manikin inside the bedding element. This view may represent the systems 10 of either FIG. 3 or 3A when in a folded up configuration.

When used as an incubator, the bedding element 12, as shown in FIG. 1-4, functions to provide insulation for an infant 100. Preferably, the bedding element 12 also functions to protect the infant 100 from the external atmosphere with regard to temperature and humidity while providing an artificial or otherwise healthy atmosphere and adequate oxygen inside the bedding element 12. The artificial atmosphere created aids in the survival and the maturing process of the infant 100. The bedding element 12 may include a hood portion 24, leg portions, arm portions, or any other suitable geometry to best enclose the infant 100.

As shown in FIGS. 3-3A, the infant 100 may first be wrapped in a cloth 22 or any other suitable material, before the infant 100 is placed in the bedding element 12. The bedding element 12 preferably wraps tightly around the infant such that when the infant 100 is enclosed in the bedding element 12, the volume of air surrounding the infant 100 is sufficiently small enough to avoid drawing moisture through the skin of the infant, which avoids the need for the regulation of humidity within the bedding element 12. Additionally, the preferred small volume allows for a close interaction between the infant 100 and its caregiver.

Referring to FIGS. 1 and 4, the bedding element 12 preferably has an inner layer 14 and an outer layer 16 that provide insulation. The inner layer 14 and outer layer 16 may be combined in a single layer or piece of material, or may include a plurality of layers or materials. The inner layer 14 and outer layer 16 are preferably washable and/or waterproof The inner layer 14 and the outer layer 16 are now further described. In a preferred variation, the inner layer 14 functions as the infant contacting layer. The inner layer 14 preferably provides insulation and is made from a non-irritant material such as cotton, nylon, or plastic-coated nylon, but may alternatively be made from any other suitable material. It is also preferred that inner layer 14 conducts heat that is supplied from the temperature regulation element as discussed later.

In a preferred embodiment, the outer layer 16 protects the infant 100 from the external atmosphere with regard to temperature and humidity, while maintaining an artificial atmosphere inside the bedding element 12. Because the outer layer 16 also protects the inner layer 14, the inner layer 14 can be made from a wider range of materials more suitable for the infant contacting layer. The outer layer 16 is preferably impermeable to water vapor and preferably provides insulation. The outer layer 16 may be made of wool, Thinsulate, nylon, fleece, Neoprene, Gortex, lycra or other suitable insulating material or combination thereof. The inner layer 14 and outer layer 16 may be any suitable layer or material to preferably provide insulation, to provide thermal conduction to the infant 100 (in the case of inner layer 14), to provide protection from the external atmosphere, and if used as an incubator, to maintain an artificial atmosphere inside the bedding element 12.

Although in FIGS. 1-4 the combination of the inner layer 14 and the outer layer 16 are shown as opaque, the inner layer 14 and the outer layer 16, or some portion thereof, may be transparent to allow for visual inspection of the infant or body to be thermally regulated. In addition, a transparent portion inner layer 14 and outer layer 16 may be preferable to allow an infant's skin to absorb the light necessary to treat the infant for jaundice through phototherapy.

As shown in FIG. 2, the system 10 may further comprise a temperature regulation element 18 thermally coupled to the bedding element 12. The temperature regulation element 18 preferably functions to maintain a temperature of the infant or body to be thermally regulated within a desired temperature range. The temperature regulation element 18 is preferably separable from the bedding element 12 thereby allowing the temperature regulation element 18 to be quickly replaced or recharged externally to the bedding element 12.

Principles of physics and the conservation of energy prevent a heat source from eternally emitting heat. Therefore, regardless of the design of the temperature regulation element 18, it will eventually stop emitting heat and will need to be recharged. Therefore, having a temperature regulation element 18 that is separable from the bedding element 12 is preferable because the temperature regulation element 18 can be easily recharged.

In addition, continuous or substantially continuous thermal regulation of the system 10 can be achieved by providing an additional temperature regulation element 18. While one temperature regulation element 18 is being used in the system 10, another temperature regulation element can be externally recharged. The temperature regulation element 18 in use can then be swapped with the additional temperature regulation element when the system 10 begins to run low on energy. This may all occur without removing the infant 100 from the bedding element 12 and thereby avoiding the risk of exposing the child to the external environment.

The thermal regulation element 18 being a separable element also provides the added benefit of allowing just the thermal regulation element 18 to be replaced if it is damaged or worn out, instead of having to replace the entire system 10. Also, providing a separate temperature regulation element 18, allows it to be recharged separately from the bedding element 12. This is important because out in the wilderness or in rural areas where electricity might not be present, recharging the temperature regulation element 18 may be performed by such methods as heating or cooling directly in water. The ability to separate the temperature regulation element 18 prevents the entire bedding element 12 from having to be involved in the recharging process and therefore opens up a broader range of recharging techniques for the thermal regulation element 18. Because the temperature regulation element 18 is removable, the recharging element can be smaller, less complicated, and make use of less sophisticated reheating techniques.

The bedding element 12 preferably includes at least two compartments. A first compartment may be formed by wrapping the inner layer 14 around the infant or body to be thermally regulated. As shown in FIG. 2, a second compartment 13 may enclose the temperature regulation element 18. In a preferred embodiment containing an inner layer 14 and an outer layer 16, the first compartment is lined with the inner layer 14 facing inward while the second compartment 13 is located between the inner layer 14 and the outer layer 16. In this preferred embodiment, the second compartment 13 can be considered a pouch, pocket, cavity or other opening between the two layers 14 and 16.

The temperature regulation element 18 may be placed in the second compartment or pocket between the inner layer 14 and outer layer 16 so that at least one surface of the temperature regulation element 18 is thermally coupled or otherwise in proximity to the first compartment containing the infant or body to be thermally regulated. This allows heat to be exchanged between the infant in the first compartment, and the temperature regulation element 18 in the second compartment 13.

In a preferred embodiment, the length of the first compartment and the length of the second compartment 13 will be approximately the same in at least one direction. This is preferably because system 10 regulates temperature more evenly if the compartments are approximately the same size, because the thermal regulation element in the second compartment 13 can provide heat along almost an entire length or a significant portion of the first compartment.

In a dual compartment, dual layer design, a bedding element 12 that can be unfolded is a preferable design for manufacturing reasons. If the bedding element 12 can be unfolded, the inner layer 14 and the outer layer 16 can be cut from different materials in a similar shape and layered together in a substantially flat form. The combined layers are then rolled or folded with the inner layer 14 facing the infant 100 to create the first compartment. As shown in FIGS. 3-3A, fasteners 26 may hold the bedding element 12 in a closed configuration.

The first compartment preferably comprises or is lined with conductive material and enclosed by the insulating material of the outer layer 16. The second compartment is formed between the inner layer 14 and the outer layer 16. The heat from the temperature regulation element 18, inside the second compartment 13, is preferably conducted into the first compartment though the inner layer 14.

The outer layer 16 preferably functions to prevent heat from escaping both the temperature regulation element 18 and the first compartment. The above described preferable design of similarly shaped inner layer 14 and outer layer 16 is a simple cost effective design to manufacture that preserves heat efficiently.

While only two layers were referenced in the above description of the bedding element 12, it is to be understood that additional layers can be added without departing from the embodiments of the present invention. In one embodiment of the thermal regulation system 10, additional removable layers may exist as part of the bedding element 12. These additional layers can be added or removed to further increase the insulation properties of the bedding element 12 to suit the external environment.

When used as an incubator, the temperature regulation element 18 of the preferred embodiments functions to maintain a body temperature of the infant 100 at or within a desired temperature range. The temperature regulation element 18 preferably maintains the body temperature of the infant 100 through conduction and also preferably maintains the temperature of the air surrounding the infant. The temperature regulation element 18 is preferably a passive element, but may alternatively actively maintain a body temperature of the infant 100. The temperature regulation element 18 preferably includes an energy storage material such as a phase change material (PCM).

A PCM is a substance which melts or solidifies at a particular temperature or temperature range thereby storing or releasing energy at that particular temperature or range. During a phase change from liquid to solid or vice versa, the energy being absorbed or released by the PCM is used to facilitate the phase change of the material and therefore, the temperature of the PCM remains constant. PCMs preferably have a high heat of fusion which allow them to store and release large amounts of energy. The ability to control temperature while releasing or absorbing large amounts of energy makes PCMs attractive for use in thermal regulation devices.

Preferably the PCM is organic because organic PCMs may provide significant advantages over inorganic PCMs. Organic PCMs are generally less toxic than inorganic PCMs. This makes organic PCMs easier to handle and work with during the manufacture of the temperature regulation element 18. The use of less toxic organic PCMs also reduces the risk of poisoning if some PCM material escapes the temperature regulation element 18 during use. In addition, organic PCMs provide increased temperature control because they are not super-cooled and therefore are not dependant on initial temperature. Increased temperature control helps avoid the risk of burns associated with the use of inorganic PCMs. Furthermore, the degradation of performance over multiple cycles of organic PCMs is much more gradual than with inorganic PCMs. This allows organic PCMs to be recharged and reused more times resulting in a longer lifespan.

Figure 2A:
Figure 2B:
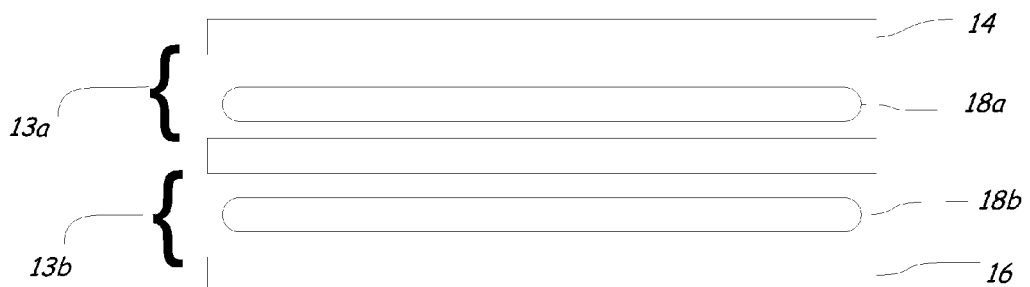

Although organic PCMs have advantages over inorganic PCMs, inorganic PCMs may still be used in the temperature regulation element 18. Furthermore, inorganic PCMs (e.g., label 18b in FIG. 2A and FIG. 2B)may be used in combination with organic PCMs (e.g., label 18a in FIG. 2A and FIG. 2B). When used in combination, it is preferable that the organic PCM (e.g., label 18a in FIG. 2A and FIG. 2B) be positioned closer to the infant than the inorganic PCM(e.g., label 18b in FIG. 2A and FIG. 2B). In this configuration, the heat released when super-cooled inorganic PCMs crystallize may be moderated by the organic PCM. The two may be in the same compartment (e.g., label 13 in FIG. 2A), or may be in separate compartments(e.g., labels 13a and 13b in FIG. 2B). If the organic PCM and inorganic PCM are in separate compartments (e.g., FIG. 2B), the heat may be transferred from the inorganic PCM to the organic PCM, which in turn passes the heat to the infant or body to be thermally regulated.

In a preferred embodiment for use as an incubator, a PCM is selected that changes phase within the desired regulation temperature range. Preferably the PCM is in liquid form above the regulation temperature range, and solid form below the regulation temperature range. The temperature regulation element 18 preferably maintains the body temperature within a narrow temperature range and, more preferably, at or about a constant or substantially constant temperature. When used as an incubator, the infant's body temperature is preferably maintained between 30 degrees Celsius and 40 degrees Celsius, and more preferably between 34 degrees Celsius and 37 degrees Celsius, or between 34 degree Celsius and 38 degrees Celsius. Suitable organic PCMs to thermoregulate an infant are n-eicosane, Tetradecanol, and eutectic mixtures but may alternatively include any other suitable material.

The temperature regulation element 18 preferably functions as both a heat source and a heat sink to passively maintain the body temperature of the infant 100. The temperature regulation element 18 is preferably heated to maintain an infant's body temperature, but may alternatively be cooled to maintain an infant's body temperature. For example, when the temperature regulation element 18 is heated in preparation for use in system 10, the PCM will melt into a liquid form. Once placed in the bedding element 12, and as the infant 100 requires heat (i.e. the infant's body temperature is lower than desired and needs to be raised), heat will transfer from the PCM to the infant 100 as the PCM solidifies and releases its latent heat of fusion in an exothermic reaction. Alternatively, the PCM may also absorb heat in an endothermic reaction if the infant's body is hotter than desired and needs to be cooled, e.g. when the infant's body temperature has risen above the desired range.

The temperature regulation element 18 preferably includes a flexible outer pouch which contains the energy storage material or PCM. The flexible outer pouch is preferably made of Polyurethane but may be made of other durable materials capable of heat transfer.

The form of the energy storage material or PCM may vary. In a first variation, the energy storage material includes a slurry of microencapsulated PCM (e.g., FIG. 2, label 19) in a liquid base(e.g., FIG. 2, label 17). In this variation, the PCM will change phases within the microcapsule casing and the liquid base will function as a heat transfer medium, distributing heat evenly. In a second variation, the energy storage material is preferably a bulk PCM. In a third variation, the energy storage material is a bulk PCM but is encased in packet size containers (e.g., FIG. 2, label 19) enclosed in the larger pouch. Similar to the microencapsulated variation, the pouch may further contain a liquid such as water (e.g., FIG. 2, label 17) to help evenly distribute the heat. Beyond the foregoing variations, the energy storage material may be any suitable material in any suitable configuration to function as a heat source and/or a heat sink.

Where the temperature regulation element 18 is configured as a pouch, the pouch may further include additives in addition to the energy transfer material and a liquid to distribute heat evenly. For example, the pouch may further contain antifungal and/or disinfectant to help prevent unwanted contamination within the pouch.

Returning again to FIG. 1, the preferred embodiments may further comprise an indicator 20 that is thermally coupled or otherwise in proximity to the temperature regulation element 18, and that functions to indicate the temperature of the temperature regulation element 18. Preferably, the indicator or some part thereof is in direct contact with the temperature regulation element 18. However, "thermally coupled" includes indirect contact between the indicator 20 and the temperature regulation element 18 such that the indicator 20 is in thermal communication with the temperature regulation element 18 and can sense the temperature.

The indicator 20 preferably changes color as the temperature regulation element 18 changes temperature, but may alternatively indicate the temperature with numbers, words, symbols, or any other suitable language or indicia to indicate temperature. For example, the indicator 20 may be blue when the temperature of the temperature regulation element 18 is too cold, green when temperature of the temperature regulation element 18 is safe (i.e. within a range of the desired body temperature), and red when temperature of the temperature regulation element 18 is too hot.

The indicator 20 may comprise different variations. In a first variation, the indicator 20 is connected to the bedding element 12 and thermally coupled to the temperature regulation element 18, when the temperature regulation element 18 is in the bedding element 12, and the system 10 is in use. The indicator 20 will preferably change color or indicia due to transfer of heat between the temperature regulation element 18 and the indicator 20, but may alternatively sense the temperature of the temperature regulation element 18 and indicate the temperature sensed.

Figure 4A:
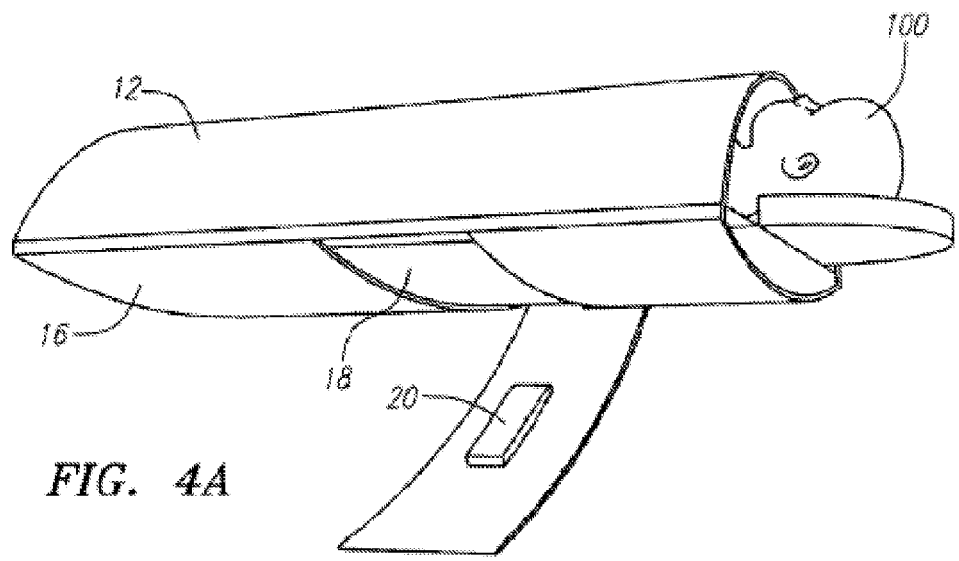
FIG. 4A, FIG. 4B, and FIG. 4C illustrate various embodiments of an exterior view with a portion or strip of the bedding element hinged open to show the temperature regulating element.
Figure 4B:
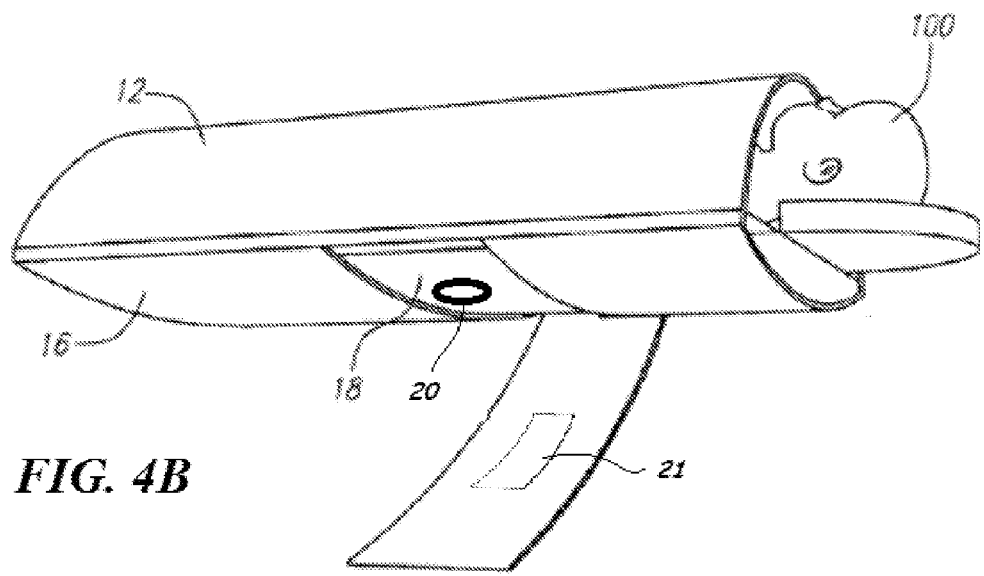

In a second variation, as shown in FIG. 1 and FIG. 4B, the indicator 20 is connected to or integrated with the temperature regulation element 18. The bedding element 12 may include a window (e.g., FIG. 4B, label 21) such that the indicator 20 can be seen through the bedding element 12 while the temperature regulation element 18 is inside the bedding element 12. In a preferred version of the second variation, the energy storage material of the temperature regulation element 18 is preferably embedded with a color changing medium that changes color in response to the temperature change of the energy storage material. The color-changing medium is preferably thermochromatic or photochromic ink, but may alternatively be any other suitable ink or color-changing medium.

Figure 4C:
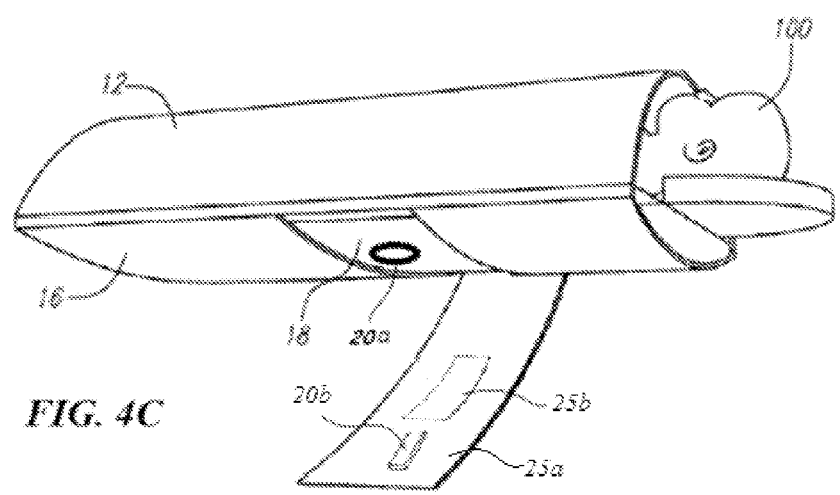

In a third variation, both the bedding element 12 and the temperature regulation element 18 may include an indicator. FIG. 4C illustrates an exterior view with a portion 25a or strip 25b of the bedding element 12 hinged open to show the temperature regulating element 18. As shown in FIG. 4C, the bedding element 12 may further comprise a portion 25a thereof or strip 25b that is completely or partially removable and allows visual inspection of the temperature regulation element 18. In this configuration the temperature of the system 10 can be checked by looking at the externally mounted indicator 20b or by removing the strip 25b or portion 25a of the bedding element 12 and visually inspecting the indicator 20a (preferably a thermochromatic ink) embedded in the thermal regulation element 18.

As shown in FIG. 4A, the indicator 20 attached to the exterior of the bedding element 12 may protrude through the bedding element 12 to directly contact the thermal regulation element 18. In addition, a portion of the bedding element 12, shown as a strip in FIG. 4A, may be partially or completely removable to allow direct inspection of the temperature regulation element 18. Although in FIG. 4A the externally mounted indicator is shown on the removable strip, this is only one embodiment and the external indicator could be mounted in a location other than on the removable portion of the bedding element 12. In addition, other combinations of indicators are possible such as an externally mounted indicator 20 in combination with an indicator embedded in the temperature regulation element 18 that may be viewed through an external window. Beyond the foregoing variations or combinations thereof, the indicator 20 may be any suitable device to indicate the temperature of the temperature regulation element 18.

In preferred embodiments such as those shown in FIGS. 1, 2, 3, and 3A, the bedding element 12 may also include fasteners 26 that function to secure the bedding element 12 around the infant or body be thermally regulated. The fasteners 26 are preferably buttons, snaps, or VELCRO, but may alternatively be any other suitable fasteners to secure the bedding element 12. In the preferred embodiment, fasteners are positioned on the bedding element 12 to accommodate varying closure positions and thereby accommodate various size infants 100 or the amount the infant 100 is enclosed.

When the system is used as an incubator, the fasteners 26 further allow the bedding element 12 to be at least partially opened to accommodate feeding the infant 100, cleaning the infant 100, skin-to-skin contact between the infant 100 and its caregiver, and/or any other suitable activity.

In a preferred embodiment, the bedding element 12 may further include additional padding and/or bedding for the infant 100. The bedding element 12 may thus function as a bed for the infant 100, but may alternatively be placed in a bed or sling worn by the infant's caregiver. The bedding element 12 is preferably designed to be used in a home and/or a clinical setting, but may additionally or alternatively be used in any other suitable setting. The bedding element 12 is preferably portable and allows for the transport of the infant 100 while the infant 100 is protected and insulated by the bedding element 12.

Figure 5:
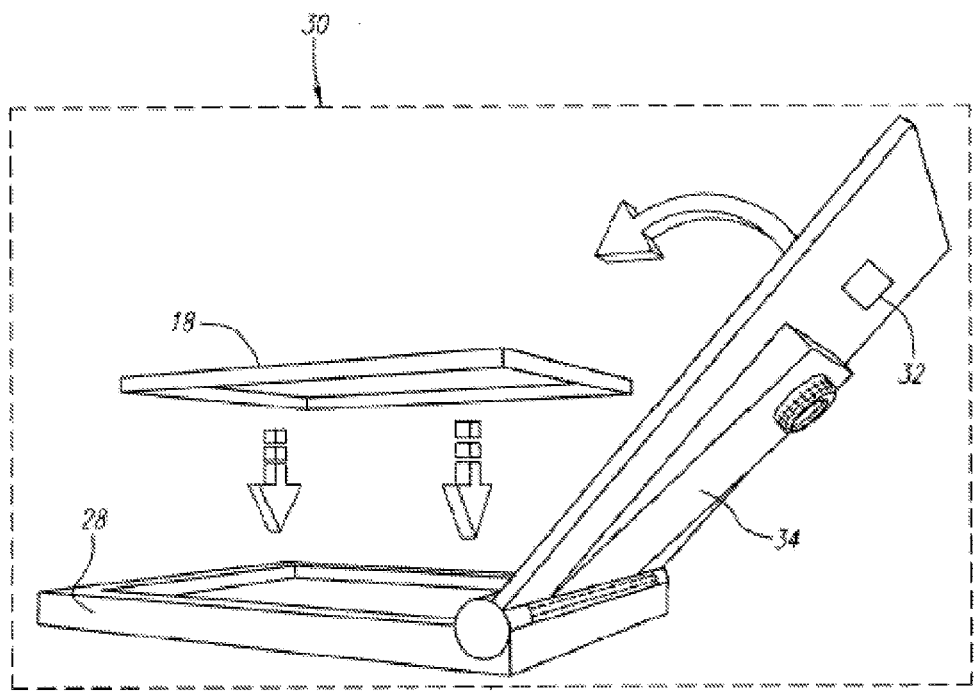
FIG. 5 illustrates a view of the recharging unit of the system according to a preferred embodiment.

FIG. 5 illustrates a view of the recharging unit 28 of the system according to a preferred embodiment. The recharging unit 28 preferably receives or otherwise couples to the temperature regulation element 18 and functions to recharge (i.e. heat or cool) the temperature regulation element 18. The recharging unit 28 preferably includes a container 34 that is filled with a hot or cold liquid, but may alternatively include an electric blanket or pouch that can be heated or cooled. The container 34 preferably has a flask shape with at least one surface having a large surface area to be coupled to the surface area of the temperature regulation element 18. The recharging unit 28 may further include an insulating sleeve 30 that wraps around the recharging unit 28 and the temperature regulation element 18 while the recharging unit 28 is recharging the temperature regulation element 18. The insulating sleeve 30 may function to retain the heat of the recharging unit 28 thereby making it more efficient. A more efficient recharging unit 28 may more quickly recharge the temperature regulation element 18 and may require less energy to do so.

The recharging unit 28 may further include an indicator 32 that functions to indicate the temperature of the temperature regulation element 18 and/or the recharging unit 28. The indicator 32 may be of various configurations. In a first variation, the indicator 32 is connected to the insulating sleeve 30 and thermally coupled to the temperature regulation element 18 when the temperature regulation element 18 is coupled to the recharging unit 28.

In a second variation, as shown in FIG. 5, the indicator 32 is connected to the recharging unit 28. In this variation, the insulating sleeve 30 may have a window through which to view the indicator 32.

In a third variation, the indicator 32 is connected to or integrated in with the temperature regulation element 18 (as described above with indicator 20). The insulating sleeve 30 includes a window such that the indicator 32 can be seen through the insulating sleeve 30 while the temperature regulation element 18 is coupled to the recharging unit 28. Beyond the foregoing variations or any combination thereof, the indicator 32 may be any suitable device to indicate the temperature of the temperature regulation element 18.

Figure 6:
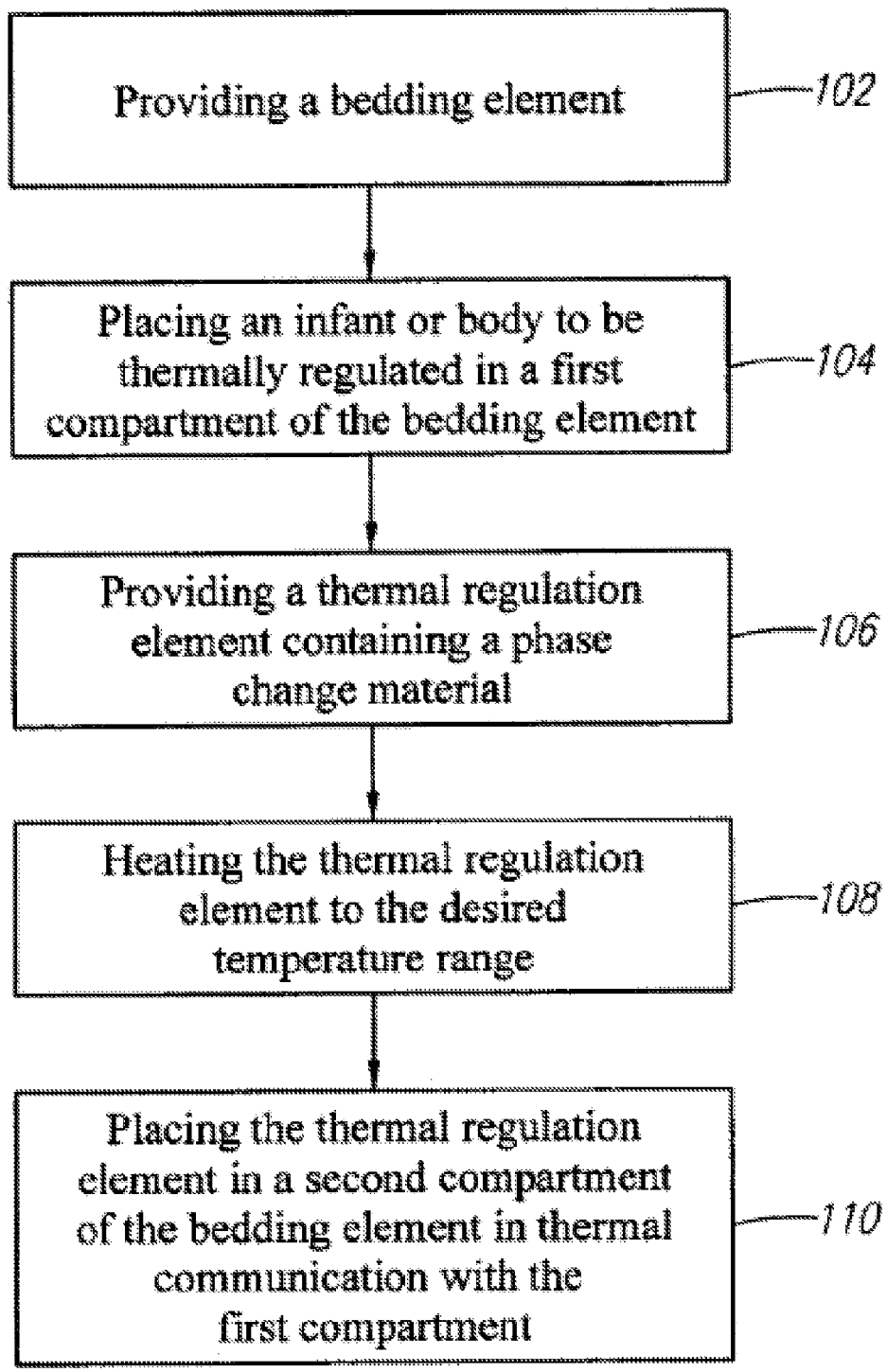
FIG. 6 illustrates a flow chart for a method of thermal regulation.

FIG. 6 illustrates a flow chart for a method of thermal regulation. As shown in FIG. 6, a method for thermal regulation with the system 10 may comprise: providing a bedding element 102; placing an infant or body to be thermally regulated in a first compartment of the bedding element 104 (which step may also include the steps of folding the flap(s) over the body portion of the bedding element); providing a thermal regulation element containing a phase change material 106; heating the thermal regulation element to the desired temperature range 108; and placing the thermal regulation element in a second compartment of the bedding element in thermal communication with the first compartment 110.

Figure 7:
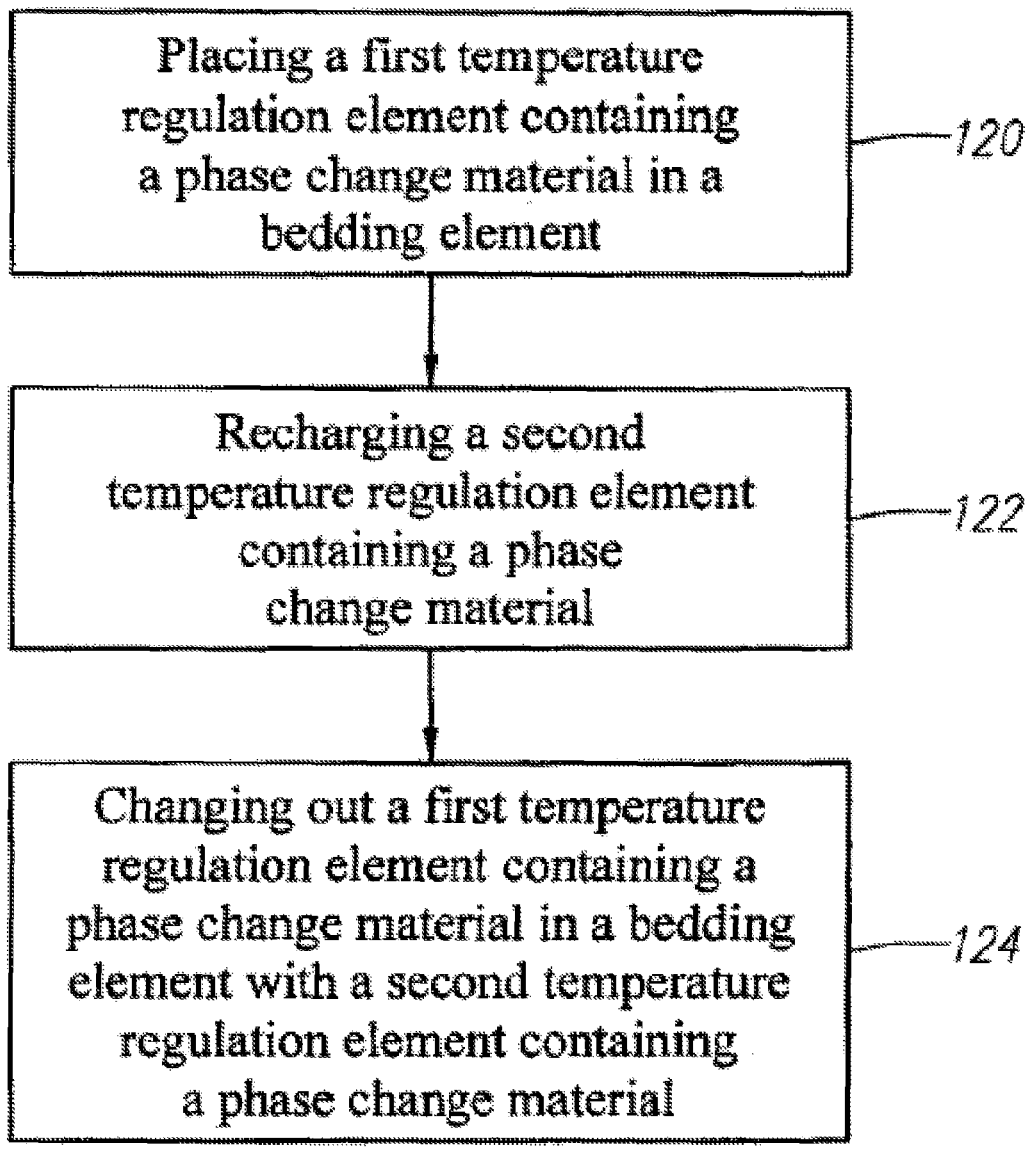
FIG. 7 illustrates a flow chart for a method of continuously heating a thermal regulation system.

FIG. 7 illustrates a flow chart for a method of continuously or substantially continuously heating a thermal regulation system. As shown in FIG. 7, the method may comprise: placing a first temperature regulation element containing a phase change material (in the desired temperature range) in a bedding element 120; recharging a second temperature regulation element containing a phase change material 122; changing out a first temperature regulation element containing a phase change material in a bedding element with a second temperature regulation element containing a phase change material 124.

Figure 8:
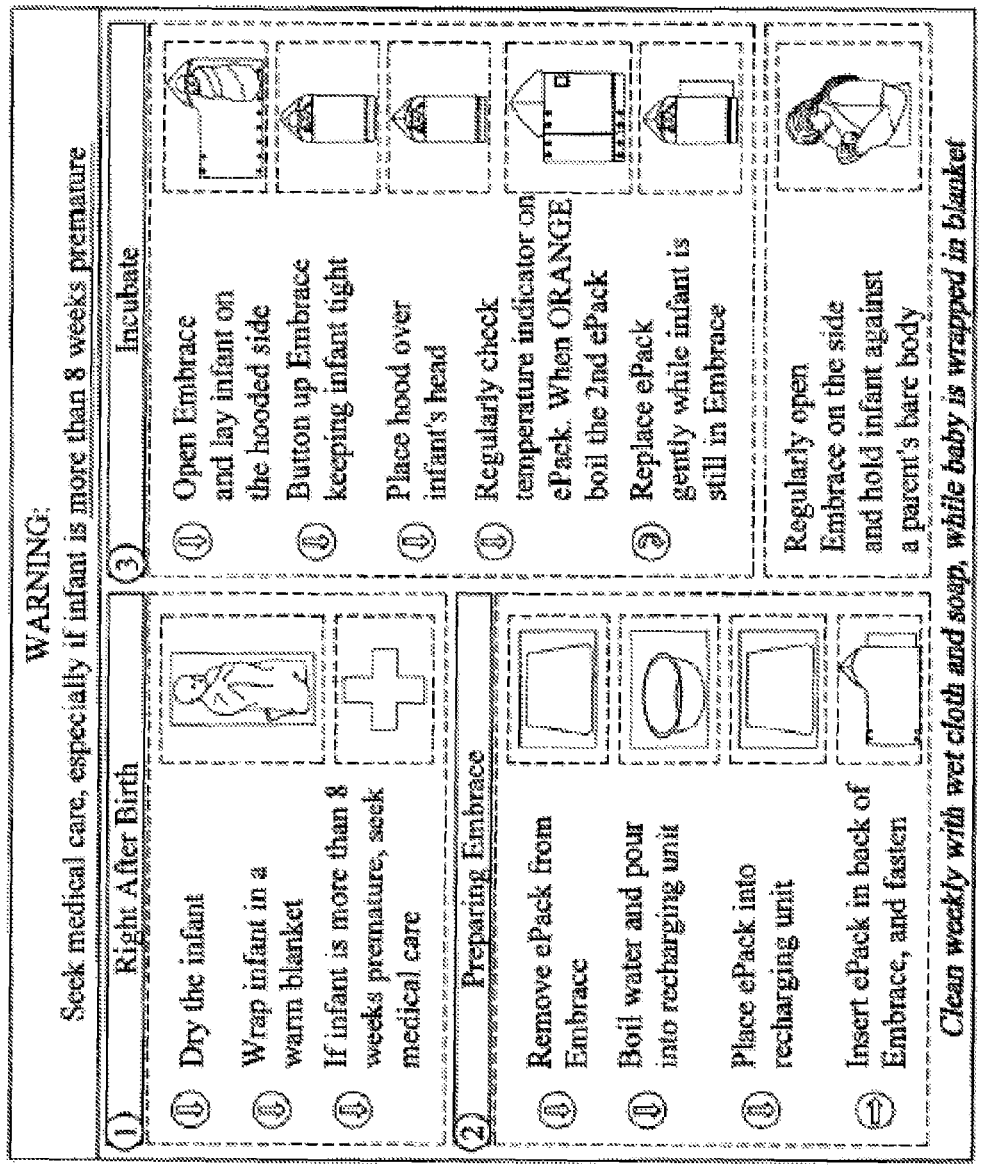
FIG. 8 illustrates steps of a method of regulating the temperature of an infant.

FIG. 8 is an instructional flyer that illustrates a method of regulating the temperature of an infant. When system 10 is used as an incubator for an infant, the method of thermo-regulating an infant with the system 10 may comprise: opening the bedding element 12, placing the infant 100 in the bedding element 12, fastening the bedding element 12 around the infant 100, verifying the temperature of the temperature regulation element 18, and placing the temperature regulation element 18 within the bedding element 12. The temperature regulation element 18 is referred to as an "ePack" in FIG. 8. When more than one thermal regulation element 18 is available, the step of placing the thermal regulation element 18 within the bedding element 12 may in fact be replacing an uncharged or depleted temperature regulation element 18 already in the bedding element 12 with a newly charged element 18. In the method of thermo-regulating an infant with the system 10, the preferred embodiments may also include the steps of opening the bedding element 12 and bringing the infant 100 in contact with its caregiver.

As shown in FIG. 8, in the method of recharging the temperature regulation element 18 of the system 10, the preferred embodiments includes: heating the temperature regulation element 18 with the recharging device 28 until hot, uncoupling the temperature regulation element 18 from the recharging device 28, waiting until the temperature regulation element 18 is the correct temperature, and inserting the temperature regulation element 18 into the bedding element 12. The caregiver may alternatively place the temperature regulation element directly in hot or cold water, rather than using the recharging device 28. To avoid a lapse in the maintenance of the body temperature of the infant 100, an additional temperature regulation element is preferably recharged before the temperature regulation element in the bedding element 12 becomes uncharged or depleted.

FIG. 8 provides additional instructions that may be used by a caregiver in post-birth care. For example, the caregiver may wish to dry the infant and wrap it in a blanket before placing the infant in the system 10. It is important to dry the infant because additional moisture on the infant's skin may make it more difficult to regulate the infant's temperature.

In addition, FIG. 8 provides a warning that all infants born more than 8 weeks premature should be taken to a medical professional. FIG. 8 may be included with the system 10 to provide instructional information regarding the use of the system 10 in post-birth care.

Although omitted for conciseness, the preferred embodiments include every combination and permutation of the various bedding elements, the various temperature regulation elements, the various indicators, the various recharging devices and the various steps and methods of use. Furthermore, the system 10 is not limited to thermo-regulating infants and it may be used for any suitable purpose. For example, the system 10 can be used to cool infants who lack oxygen to reduce the risk of brain damage and cerebral palsy.

As further examples, the system 10 can be used in disaster relief situations or in cold areas to prevent hypothermia, and/or for military purposes such as warming soldiers in cold weather conditions or for tasks like keeping food warm or thermo-regulating inanimate objects.

As a person skilled in the art will recognize from the previous detailed description and from the figures and claims, modifications and changes can be made to the preferred embodiments of the invention without departing from the scope of this invention defined in the following claims.

What is claimed is:

1. A system for regulating temperature within a desired temperature range, comprising:
    a bedding element that is configured to enclose at least a part of a living being; and
    a first temperature regulation element that includes an organic phase change material which changes between a liquid phase and a solid phase within the desired temperature range, wherein said organic phase change material is encased in containers enclosed in a larger pouch that contains a liquid;
    a second temperature regulation element that includes an inorganic phase change material which changes between a liquid phase and a solid phase within the desired temperature range, wherein said inorganic phase change material is encased in containers enclosed in a larger pouch that contains a liquid;
    wherein the first temperature regulation element and the second temperature regulation element are included in the bedding element and are individually separable from the bedding element while the bedding element continues to enclose the living being.

2. The system of claim 1, wherein the first temperature regulation element is positioned closer to the living being than the second temperature regulation element.

3. The system of claim 1, wherein the bedding element includes a compartment and both the first temperature regulation element and the second temperature regulation element are contained in the compartment.

4. The system of claim 1, wherein the bedding element includes a first compartment that contains the first temperature regulation element and a second compartment that contains the second temperature regulation element.

5. A system for regulating temperature within a desired temperature range, comprising:
    a bedding element that is configured to enclose at least a part of a living being;
    a temperature regulation element that is included in the bedding element and that includes a phase change material which changes between a liquid phase and a solid phase within the desired temperature range, wherein said phase change material is encased in containers enclosed in a larger pouch that contains a liquid; and
    a temperature indicating element in communication with the system;
    wherein the temperature regulation element is separable from the bedding, element while the bedding element continues to enclose the at least a part of a living being.

6. The system of claim 5, wherein the temperature indicating element is connected to the bedding element and thermally coupled to the temperature regulation element.

7. The system of claim 5, wherein the temperature indicating element is connected to the temperature regulation element.

8. The system of claim 7, wherein the bedding element includes a window through which the temperature indicating element is visible.

9. The system of claim 7, wherein the bedding element includes a removable portion that upon removal renders the temperature indicating element visible.

10. The system of claim 7, further comprising:
a recharging unit that is separate from the bedding element;
wherein the recharging unit is configured to receive and recharge the temperature regulation element when the temperature regulation element is separated from the bedding element; and
wherein the recharging unit includes a window through which the temperature indicating element is visible.

11. The system of claim 7, further comprising:
a recharging unit that is separate from the bedding element, wherein the recharging unit is configured to receive and recharge the temperature regulation element when the temperature regulation element is separated from the bedding, element; and
an insulating sleeve that encloses the recharging unit, wherein the insulating sleeve includes a window through which the temperature indicating element is visible.

12. The system of claim 5, further comprising:
a second temperature indicating element that is connected to the temperature regulation element;
wherein the temperature indicating element is connected to the bedding element.

13. The system of claim 12, wherein the bedding element includes a window through which the second temperature indicating element is visible.

14. The system of claim 12, wherein the bedding element includes a removable portion that upon removal renders the second temperature indicating element visible.

15. The system of claim 12, further comprising:
a recharging unit that is separate from the bedding element;
wherein the recharging unit is configured to receive and recharge the temperature regulation element when the temperature regulation element is separated from the bedding element; and
wherein the recharging unit includes a window through which the second temperature indicating element is visible.

16. The system of claim 12, further comprising:
a recharging unit that is separate from the bedding element, wherein the recharging unit is configured to receive and recharge the temperature regulation element when the temperature regulation element is separated from the bedding, element; and
an insulating sleeve that encloses the recharging unit, wherein the insulating sleeve includes a window through which the second temperature indicating element is visible.

17. The system of claim 5, further comprising:
a recharging unit that is separate from the bedding element;
wherein the recharging unit is configured to receive and recharge the temperature regulation element when the temperature regulation element is separated from the bedding element; and
wherein the recharging unit includes the temperature indicating element; and
wherein the temperature of the system displayed by the temperature indicating element is indicative of a temperature of the temperature regulation element when the temperature regulation element is received by the recharging unit.

18. The system of claim 17, further comprising an insulating sleeve that encloses the recharging unit, wherein the insulating sleeve includes a window through which the temperature indicating element is visible.

19. The system of claim 5, further comprising:
a recharging unit that is separate from the bedding element, wherein the recharging unit is configured to receive and recharge the temperature regulation element when the temperature regulation element is separated from the bedding element and
an insulating sleeve that encloses the recharging unit, wherein the insulating sleeve includes the temperature indicating element;
wherein the temperature of the system displayed by the temperature indicating element is indicative of a temperature of the temperature regulation element when the temperature regulation element is received by the recharging unit.

\* \* \* \* \*